(12) United States Patent
Allen et al.

(10) Patent No.: US 8,110,106 B2
(45) Date of Patent: Feb. 7, 2012

(54) ANAEROBIC DIGESTER DESIGN AND OPERATION

(75) Inventors: Stephen D. Allen, Eagle, ID (US); Dallas K. Isom, Middleton, ID (US)

(73) Assignee: Water Solutions, Inc., Sioux Falls, SD (US)

( * ) Notice: Subject to any disclaimer, the term of this patent is extended or adjusted under 35 U.S.C. 154(b) by 374 days.

(21) Appl. No.: 12/539,293

(22) Filed: Aug. 11, 2009

(65) Prior Publication Data

US 2010/0032370 A1 Feb. 11, 2010

Related U.S. Application Data

(60) Provisional application No. 61/094,619, filed on Sep. 5, 2008, provisional application No. 61/087,904, filed on Aug. 11, 2008.

(51) Int. Cl.
*C02F 11/02* (2006.01)
*C02F 3/30* (2006.01)

(52) U.S. Cl. ........ 210/603; 210/613; 210/630; 210/631; 210/610; 210/259

(58) Field of Classification Search ................. 210/603, 210/610, 611, 612, 613, 630, 631, 252, 259
See application file for complete search history.

(56) References Cited

U.S. PATENT DOCUMENTS

| | | | | |
|---|---|---|---|---|
| 4,246,099 A | * | 1/1981 | Gould et al. | 210/603 |
| 4,325,823 A | * | 4/1982 | Graham | 210/86 |
| 4,392,881 A | * | 7/1983 | Kneer | 71/9 |
| 4,915,840 A | * | 4/1990 | Rozich | 210/605 |
| 5,578,202 A | * | 11/1996 | Hirane | 210/150 |
| 6,673,243 B2 | * | 1/2004 | Srinivasan et al. | 210/532.2 |
| 6,767,464 B2 | * | 7/2004 | Boyd et al. | 210/610 |
| 2006/0289356 A1 | * | 12/2006 | Burnett et al. | 210/603 |
| 2008/0073266 A1 | * | 3/2008 | McWhirter et al. | 210/605 |
| 2008/0314806 A1 | * | 12/2008 | Okamoto | 210/85 |

FOREIGN PATENT DOCUMENTS

| | | | |
|---|---|---|---|
| JP | 2006-314991 A | * | 11/2006 |
| KR | 10-2002-0073781 A | | 9/2002 |
| KR | 10-0479649 B1 | | 4/2005 |
| KR | 10-0485639 B1 | | 4/2005 |
| WO | 02/15945 A1 | | 2/2002 |

OTHER PUBLICATIONS

International Search Report for PCT/US2009/053427, Korean Intellectual Property Office, Mar. 26, 2010.

\* cited by examiner

*Primary Examiner* — Fred Prince
(74) *Attorney, Agent, or Firm* — Kirton & McConkie; Evan R. Witt (57) ABSTRACT

An apparatus for the anaerobic digestion of solid waste is disclosed. The apparatus includes a pre-digestion treatment chamber and an anaerobic digester chamber coupled to the pre-digestion treatment chamber. A liquid suspension of solid waste is pretreated under aerobic conditions by heating to a desired pre-digestion temperature. One or more chemical or biological additives are added to the suspension of solid waste to improve the anaerobic digestibility of the solid waste. This may include enzymes to destruct poorly digestible solids and/or materials to provide a desired C:N ratio in the solid waste. The apparatus may include mixers, heaters, chemical or biological additives as needed, various sensors and probes, and a control system to monitor and control the anaerobic digestion process and maintain microbial health of the digester.

50 Claims, 3 Drawing Sheets

ANAEROBIC DIGESTER DESIGN AND OPERATION

CROSS-REFERENCE TO RELATED APPLICATIONS

This application claims the benefit of U.S. Provisional Patent Application No. 61/087,904, filed Aug. 11, 2008 and U.S. Provisional Patent Application No. 61/094,619, filed Sep. 5, 2008, which applications are incorporated by reference.

FIELD OF THE INVENTION

The present invention is directed to an anaerobic digester design and to operation of anaerobic digesters. More specifically, the present invention relates to innovative pre-digestion conditioning of the solid waste to improve anaerobic digestion operation and efficiency. The present invention further relates to an anaerobic digester that permits active monitoring and control of the anaerobic digestion process.

BACKGROUND OF THE INVENTION

In recent years, anaerobic digesters are proliferating in the United States and abroad. The growth of the industry is increasing in popularity as the carbon credits and "manure to power" industry has evolved and grown. The creation of energy (electrical conversion and heat) from methane generated by the anaerobic conversion of organic matter in the wastewater has been documented and is well understood.

There are currently over a hundred operational anaerobic digesters located in the United States and/or a far greater number in Europe, Canada and South America. The industries to which this technology would apply include, but are not limited to, dairies, bovine confinement, porcine confinement and birthing processes, poultry confinement, industrial processes where anaerobic digestion is employed, such as animal processing, food, ethanol and general food processors where a digestible wastewater is generated.

The key process stages of anaerobic digestion include hydrolysis, acidogenesis, acetogenesis, and methanogenesis. The microbial health of an anaerobic digester affects these processes and the overall performance of the digester. Bacterial hydrolysis of insoluble organic material occurs initially, followed by acidogenic bacteria which convert sugars and amino acids into carbon dioxide, hydrogen, ammonia, and organic acids. Acetogenic bacteria convert organic acids into acetic acid and additional decomposition products ammonia, hydrogen, and carbon dioxide. Finally, methanogens convert these products into methane and carbon dioxide. Different species of bacteria are able to survive at different temperature ranges. Bacterial that live optimally at temperatures between about 95°-105° F. (35.0° C.-40.6° C.) are called mesophiles or mesophilic bacteria. Some bacteria can survive at hotter temperatures of 125°-135° F. (51.7° C.-57.2° C.) are called thermophiles or thermophilic bacteria.

Anaerobic digestion (AD) may occur in the ambient psychrophilic temperature range routinely observed in the impoundment of treatment lagoons for cows. Conventional anaerobic digesters (ADs) are commonly designed to operate (primarily) in either the mesophilic temperature range or in the thermophilic temperature range noted above. There are usually two reasons why the mesophilic and thermophilic temperatures are preferred. One, a higher loading rate of organic materials can be processed and because a higher retention time (or HRT) is associated with higher temperatures, increased methane outputs for a given digester capacity result. Second, higher temperatures can increase the destruction of pathogens present in the raw manure.

In addition to the temperature, another major consideration is the type of flow through the AD. There are several different types of digesters based on the type of flow, such as fixed film, biphasic orbicular (plug flow and fixed film), upflow anaerobic sludge blanket (UASB), and plug flow to name but a few. One example of a plug flow digester that has met with success is a plug flow digester provided by GHD, Inc. of Chilton, Wis. Details of this digester are disclosed in U.S. Pat. Nos. 6,451,589, 6,613,562, 7,078,229, and 7,179,642. A need, however, exists to improve the digestibility of the solids, to convert more of the organic moieties to methane, and to reduce chemical oxygen demand (COD). Many, most notably, the fixed film digesters, have touted the ability to destruct more solids for the formation of methane, a yield which, theoretically, results in more biogas (methane) per unit of volume and time. However, the theory and the practice do not match and results thus far have been dismal.

Anaerobic digestion can be accomplished with fluid flow of varying types, either direct, as in a conventional plug flow (pushing the solids throughout the length of the digester), an upflow type such as a fixed film (additions form the base flowing up and then down in a directed manner), or sludge blanket types of upflow and directed, only without the use of numerous plates, simply a sludge blanket as the collection area for the bacteria growth and collection. Fixed film and UASB use bacteria growth media and collection to speed up the process. Plug flow uses time as the primary growth medium.

The concentration of solids into a digester is an important factor of the economic decisions on digester type. A high solids, high flow system cannot be used in most digesters, it is simply economically not feasible. For example, a fixed film digester cannot receive more than 7% solids as an influent feed. At 250 gallons per minute assuming a 10% solids feed, and a 7 day retention time, the volume of liquid to be retained is 3,600,000 gallons. A plug flow digester with 21 days retention time requires finding a source of more concentrated waste to bring the solids up to 12%, the recommended concentration for feed to the digester. Under those conditions, the volume to be retained is 7,560,000 gallons. A fixed film digester is constructed of above-ground, glass-lined steel tanks. A plug flow digester is constructed of below ground concrete bunkers. Given the present construction costs for the above ground design for the fixed film and the concrete bunker design for the plug flow, the plug digester may be fabricated at a substantially lower cost per unit of volume compared to the fixed film digester.

Mixing is another of the parameters that affects the performance of the digester. Continuous mixing is important for a variety of reasons, not the least of which is the contact required for the bacteria and the enzymatic reactions to take place. Contact time is a factor, but not nearly as important as the mixing of the solids and the liquid phases. Some anaerobic digester technology employs a gas mixing method, other digester technology use directed flows for mixing and turbulent actions throughout (such as cascading) for the mixing. Additional factors impact the performance of a digester in producing methane, e.g. height of the digester, length, width, gas collection area, etc.

Anaerobic digesters are generally designed and optimized to digest a specific type of source material. Digesters designed for one type of solid waste material usually operate at much lower efficiency when attempting to digest other types of solid waste material. For example, an anaerobic digester optimized to digest one type of waste solid, such as cattle manure, may not be effective to digest another type of waste solid, such as ethanol fermentation waste solids, dairy waste solids, or pharmaceutical biological waste solids. Even subtle changes in the type of source material affect the digester operation and performance. As an example, a digester designed to digest cattle and dairy cow manure will not operate as effectively to digest other types of manure, such as chicken and hog manure.

Healthy and abundant microbes are expected to destruct larger quantities of waste solids and generate larger quantities of methane gas. The microbial health of an anaerobic digester can be affected by variation of source material being digested, microbial nutrition, temperature variations within the digester, pH changes within the digester, and so forth. The effectiveness of an anaerobic digester may be evaluated based upon the amount of methane generated and upon the destruction of waste solids. Digester effluent waste solids are characterized by size, such as suspended solids (<10 µm in size) and the so-called "bedding" solids (>10 µm in size). An effectively operated anaerobic digester produces an effluent with low solids content.

Anaerobic digesters usually operate within a narrow temperature range, which in many geographical locations is hotter than normal ambient temperatures. In cooler seasons, the source material is often at a temperature much lower than the digester operating temperature. As a cool suspension of waste solids (source material) is introduced into the warm solid suspension within the digester, a temperature differential or thermocline may develop. Under such conditions, solids have been known to precipitate or settle within the digester at the beginning of the process. Settling has also been known to occur later on in the digester process by even small temperature differentials within a digester. Such settling can cause short circuiting and channeling of the digester fluids. Short circuiting and channeling substantially reduce and may even prevent effective operation of the anaerobic digester.

In view of the foregoing, it would be an improvement in the art to provide an anaerobic digester that minimizes temperature differentials and associated solid settling, channeling and short circuiting. It would be a further improvement in the field of anaerobic digestion to provide a digester design that improves mixing and temperature control and increases the yield of methane gas generated from the anaerobic digestion of solids.

It will be appreciated that there is also a need in the art for an anaerobic digester that provides effective control and maintenance of microbial health within the digester. It would be another advancement in the art to provide an anaerobic digester that permits effective digestion of a variety of source material waste solids so that the digester may be efficiently used and managed.

A need exists in the field of anaerobic digestion for a digester that has the capacity for increasing the yield of methane gas generated from the anaerobic digestion of solids, either from waste or direct digestion of products and by-products. There is also a need in the art for an anaerobic digester that more effectively destructs waste solids.

SUMMARY OF THE INVENTION

The present invention is drawn to anaerobic digester designs and operation methods that improve the yield and operation effectiveness of anaerobic digesters. While the following discussion will focus on a plug flow design for an anaerobic digester, it will be understood by persons having ordinary skill in the art that certain design features and process steps and conditions may be adapted for use with other digester designs, including but not limited to fixed film, upflow anaerobic sludge blanket (UASB), and cross over technologies such as biphasic orbicular biodigesters (BOB), a modified fixed film and plug flow design.

In certain embodiments within the scope of the present invention, an apparatus for the anaerobic digestion of solid waste includes a pre-digestion treatment chamber. The pre-digestion treatment chamber provides heating, aerobic treatment, and conditioning of a liquid suspension of solid waste. The term pre-digestion treatment chamber is intended to include related structures and parts that may not be physically disposed within a given pre-digestion treatment chamber, but are attached to or connected to the pre-digestion treatment chamber.

The pre-digestion treatment chamber operates under aerobic conditions. It may be open to the atmosphere. The pre-digestion treatment chamber comprises one or more inlets to add one or more chemical or biological additives as needed to the suspension of solid waste. The chemical or biological additives are selected to improve the anaerobic digestibility of the solid waste. Such additives may include, but are not limited to, pH control chemicals, inoculums, enzymes, surfactants, nutritional additives to support microbial health within the digester, additives to facilitate the pre-destruction of poorly digested waste solids, and so forth.

It has been observed that certain waste solids are often poorly digested. Such poorly digested waste solids may be rendered digestible by pre-digestion treatment with one or more enzymes. Non-limiting examples of poorly digested waste solids include, but not limited to, certain cellulosic, fatty acid, lignin based waste materials. In such cases, one or more appropriate enzymes, such as, but not limited to, a cellulase, hemicellulase, lipase, protease, ligninase, laccases, and/or urease enzyme, may be added to the pre-digestion treatment chamber. The pH, temperature, residence time, and other factors may be controlled to improve the pre-digestion treatment of poorly digested waste solids.

The pre-digestion treatment chamber may include one or more chemical sensors to measure total carbon and total nitrogen content of the suspension of solid waste. Chemical sensors may also be provided to measure total phosphorus content and pH of the solid waste. It is within the scope of persons having ordinary skill in the art to utilize other chemical sensors as needed in the pre-digestion treatment chamber to measure and monitor useful physical or chemical properties of the suspension of waste solids. It is within the scope of the invention to connect such sensors to a control unit to provide automation and control of pre-digestion processes, including addition of chemical or biological additives, temperature, flow rates, and so forth.

One or more chemical sensors may be used to measure the carbon to nitrogen (C:N) ratio in the solid waste source material. The C:N ratio is preferably maintained in the range from about 15:1 to about 25:1, and preferably from about 20:1 to 25:1. In some exceptional high carbon cases, the ratio may approach 65:1, but in most applications, the C:N ratio is maintained at a level which permits good microbial heath within the anaerobic digester to accomplish both solids destruction and methane gas generation. If the nitrogen content is too high, more ammonia tends to be formed in the anaerobic digester. Too much ammonia can lead to high pH levels in the digester (pH of 7.8-8.2, or higher) which, if uncorrected, can destroy the methanogenic bacteria and seriously disrupt methane gas generation. Similarly, if the carbon content is too high, too much lactic acid and other organic acids are generated which lower the pH within the digester.

Low pH conditions can also kill methanogenic bacteria and disrupt methane gas generation.

Regular monitoring the C:N ratio of the suspension of solid waste allow, including real time monitoring, may permit one to adjust and maintain a desired C:N ratio of the solid waste. For example, if needed a carbon-rich waste product may be added to increase the carbon content of the solid waste. Similarly, if needed a nitrogen-rich material to increase the nitrogen content of the solid waste. The monitoring and control of the C:N ratio may be automated using a suitable control unit.

The pre-digestion treatment chamber includes a heater to heat a liquid suspension of solid waste to a desired pre-digestion temperature. A variety of different heater configurations may be used including, but not limited to a sleeve heater, in-line heater or a heater provided within the walls of the pre-digestion treatment chamber. The heater may be integral or separate from the pre-digestion treatment chamber. In some non-limiting embodiments, the heater heats the liquid suspension of solid waste to a temperature in the range from about 85° to about 150° F.

The pre-digestion treatment chamber treatment chamber is sized to provide adequate treatment and conditioning time to the suspension of solid waste. The pre-digestion treatment chamber may have a volume equivalent selected to provide a retention time in the range from approximately 8 hours to 48 hours based upon the flow rate of the liquid suspension of solid waste. In some embodiments, the pre-digestion treatment chamber may be sized to have a retention time from approximately 18 hours to 36 hours.

The apparatus for the anaerobic digestion of solid waste includes an anaerobic digester chamber. In some embodiments, it is coupled to the pre-digestion treatment chamber at a digester chamber inlet to receive the pre-treated liquid suspension of solid waste. The anaerobic digester chamber will typically include a floor, walls, and a ceiling, a digester chamber outlet where a suspension of digested waste solids exit the digester, and one or more gas collection ports to collect gas produced in the anaerobic digester.

The apparatus for the anaerobic digestion of solid waste within the scope of the present invention may include other features to improve the yield, efficiency, and performance of the digester.

The anaerobic digester chamber may include heating elements embedded within the floor, walls, and optionally ceiling. The heating elements may be designed to heat specific zones or regions of the digester. A plurality of temperature sensors may be dispersed throughout the anaerobic digester chamber. A control system may be coupled to the temperature sensors and heating elements to provide continuous, regulated heating of the anaerobic digester chamber.

In some non-limiting embodiments, the temperature of the anaerobic digester chamber is regulated to a temperature in the range from about 90° F. to 145° F. (32.2° C. to 62.8° C.). In other non-limiting embodiments, the temperature of the anaerobic digester chamber is regulated to a temperature in the range from about 90° F. to 110° F. (32.2° C. to 43.3° C.). In still other non-limiting embodiments, the temperature of the anaerobic digester chamber is regulated to a temperature in the range from about 120° F. to 145° F. (48.9° C. to 62.8° C.).

The anaerobic digester chamber may include a plurality of mixers dispersed throughout the anaerobic digester chamber to mix the suspension of solid waste. Non-limiting examples of mixers include peristaltic hose pumps and variable speed mixers. In some embodiments within the scope of the invention, the mixing is slow near the inlet and progressively becomes faster near the outlet. Thus, mixers disposed closest to the digester chamber inlet may operate at a slower speed than the mixers disposed closest to the digester chamber outlet.

The anaerobic digester chamber may include a plurality of chemical inlets to inject one or more chemical or biological additives at desired locations within the anaerobic digester chamber. Non-limiting examples of such additives include acids or bases for pH control, microbial innoculum, nutrients to support microbial growth, defoaming and/or antifoaming agents, water, and so forth. Some non-limiting examples of nutrients which support microbial growth include free amino acid nitrogen (FAN), metals cations such as calcium, zinc, copper, and so forth. Certain metal cations may also be added to facilitate enzyme activity and to provide "food", along with the amino acids, for microbial growth. In some embodiments, the chemical inlets may be configured as a liquid spray system disposed at the ceiling.

The anaerobic digester chamber may include a plurality of pH sensors dispersed throughout the anaerobic digester. The plurality of chemical inlets are preferably coupled to the control system and introduce acid or base to the suspension of solid waste to control the pH based upon pH measurements from the pH sensors. In a typical anaerobic digester process, the pH is preferably maintained in the range from about 5 to 9. The actual pH may vary depending upon the source of waste solid. As an example, animal waste digestion may operate at a pH range from about 7.1 to 7.6, for corn ethanol solids, the pH may range around 5.2, and for cane solids the pH may range around 6 or slightly higher. An important benefit of this pH control system is the ability to monitor and control pH within various regions of the digester chamber in real time. Prior art pH control techniques require days and sometimes weeks to control pH conditions within the digester.

Other sensors may be dispersed throughout the digester as needed and coupled to the control system to monitor the digester operation and make appropriate changes to digester operation, such as addition of appropriate chemical or biological additives.

The anaerobic digester chamber may include a drain disposed in the floor of the digester chamber adjacent the digester outlet. To facilitate drainage, the floor is preferably sloped towards the drain. A drainage system, coupled with the ability to introduce water into the digester chamber, enables the entire anaerobic digester to be flushed and drained. This is important in circumstances where the entire content of the anaerobic digester needs to be flushed and replaced.

In some embodiments, the anaerobic digester chamber may include a recycle conduit connecting the last quadrant of the digester chamber to the first quadrant of the digester chamber. Recycling a portion of the suspended solids of the nutrient and bacterial loads may improve anaerobic digestion of the suspended solids.

To improve mixing a solids flow through the anaerobic digester chamber, a plurality of triangular deflecting plates may be disposed along the walls of the digester. The triangular deflecting plates preferably have a surface that provides points of attachment for bacteria.

In embodiments where the anaerobic digester chamber is configured for plug flow of the suspension of solid waste, the anaerobic digester chamber preferably has a length to width ratio in the range from 4:1 to 9:1.

In certain embodiments the process for the anaerobic digestion of solid waste includes the steps of preheating a liquid suspension of solid waste, exposing the suspension of solid waste to aerobic conditions in a pre-digestion treatment chamber, and adding one or more chemical or biological additive as needed to the suspension of solid waste in the pre-digestion treatment chamber to provide a desired C:N ratio in the solid waste and/or to destruct a poorly-digestible component of the solid waste. Information regarding what chemical or biological additive to add may be obtained by chemical analysis of the solid waste feed and/or analysis of the non-digested solids upon completion of anaerobic digestion.

In some embodiments within the scope of the invention, the anaerobic digestion process may include measuring total carbon and total nitrogen content of the solid waste in the pre-digestion treatment chamber. A carbon-rich waste product may be added, as needed, to increase the carbon content of the solid waste. In other cases a nitrogen-rich material may be added, as needed, to increase the nitrogen content of the solid waste.

In some embodiments, one or more enzymes may be added to the suspension of waste solids which are selected to destruct the poorly-digestible component of the suspended waste solids. Non-limiting examples of typical enzymes cellulase, hemicellulase, lipase, protease, ligninase, laccase, and urease. In other embodiments, a surfactant may be added to the suspension of waste solid in the pre-digestion treatment chamber. Surfactants (surface active agents) aid in prompting destructive processes by allowing enzymes to penetrate into interstitial spaces below the 0.02 micron levels.

The process for the anaerobic digestion of solid waste includes introducing the suspension of solid waste into an anaerobic digester to anaerobically digest the solid waste. The may include controlling the temperature of the suspension of solid waste in the anaerobic digester to a temperature in the range from about 90° F. to 145° F. (32.2° C. to 62.8° C.). The process may also include mixing the suspension of solid waste as it passes through the digester. Non-limiting examples of mixing are discussed above. In some embodiments, the process includes controlling the pH of the suspension of solid waste in the anaerobic digester to a pH in the range from about 5 to 9.

Because an important purpose of the anaerobic digester is to produce methane gas, the process for the anaerobic digestion of solid waste includes recovering methane gas produced by the anaerobic digester.

The process may further include removing non-digested solids from the anaerobic digester and analyzing the non-digested solids to identify any poorly-digestible components. This information may be used to select chemical or biological additives to destruct the poorly digestible component within the pre-digestion treatment chamber.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment, but may refer to every embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of structural features of anaerobic digesters, process conditions, chemical and biological additives, etc., to provide a thorough understanding of embodiments of the invention. One having ordinary skill in the relevant art will recognize, however, that the invention may be practiced without one or more of the specific details or method steps, or with other methods, components, materials, and so forth. In other instances, well-known structures, materials, or operations are not shown or described in detail to avoid obscuring aspects of the invention.

Figure 1:
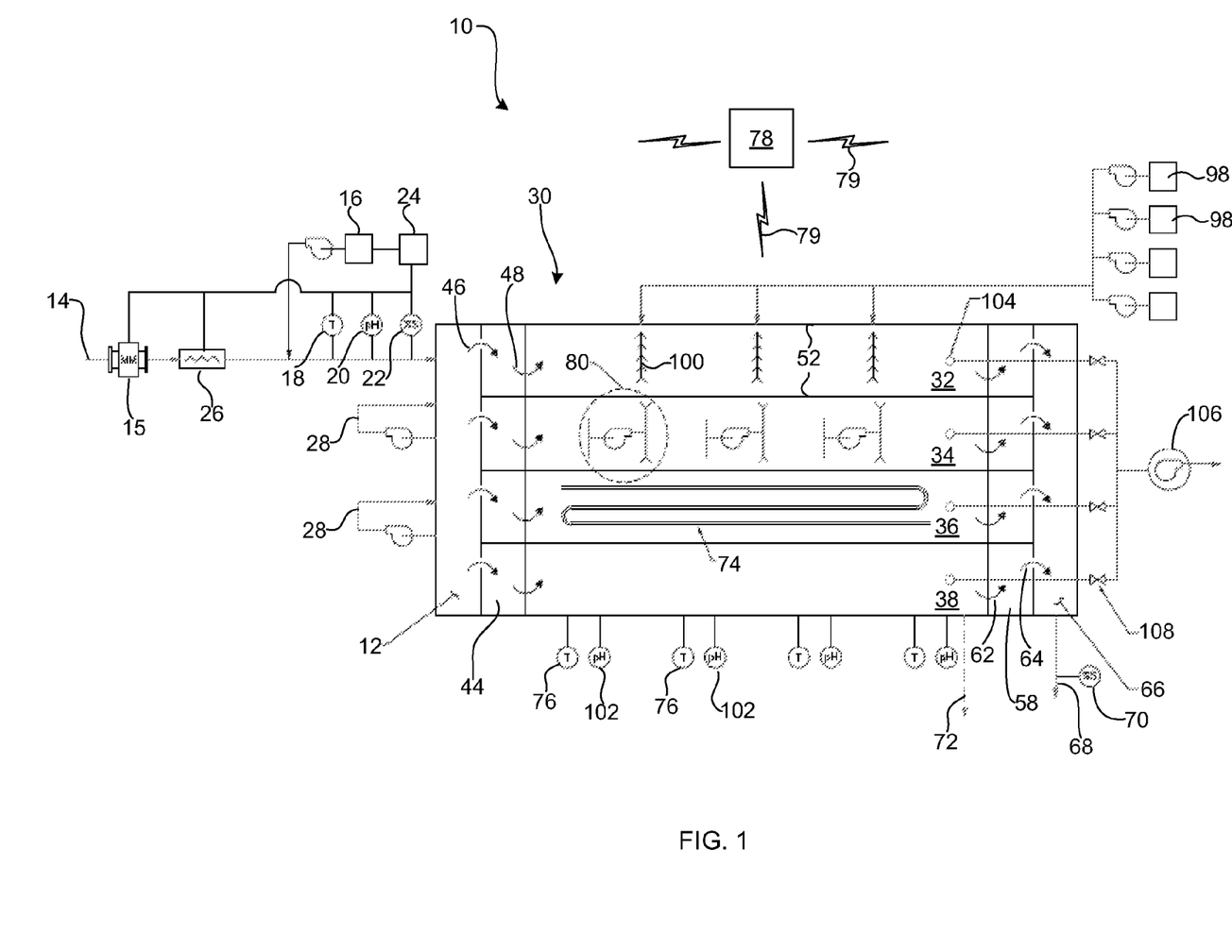
FIG. 1 is a schematic representation of an apparatus for the anaerobic digestion of solid waste.

Reference is made to FIG. 1. FIG. 1 discloses a schematic representation of an apparatus for the anaerobic digestion of solid waste 10. The apparatus 10 includes a pre-digestion treatment chamber 12. The pre-digestion treatment chamber 12 provides heating, aerobic treatment, and conditioning of an influent liquid suspension of solid waste 14. The influent 14 can be from any source of digestible solid waste, such as those discussed above. A flow meter 15 may be provided to provide influent flow information. The pre-digestion treatment chamber 12 operates under aerobic conditions.

The pre-digestion treatment chamber 12 comprises one or more inlets 16 to add one or more chemical or biological additives as needed to the suspension of solid waste. As discussed above, the chemical or biological additives are selected to improve the anaerobic digestibility of the solid waste. They may include, but are not limited to, pH control chemicals, inoculums, enzymes, surfactants, nutritional additives to support microbial health within the digester, additives to facilitate the pre-destruction of poorly digested waste solids, and so forth.

The pre-digestion treatment chamber may include one or more sensors. Non-limiting examples of such sensors shown in FIG. 1 include temperature sensor 18, pH sensor 20, and waste solids analysis sensor(s) 22 which may measure total carbon, total nitrogen, total phosphorous, percent solids, and so forth. It is within the scope of the invention to connect such sensors to a control unit 24 to provide automation and control of pre-digestion processes, including addition of chemical or biological additives, temperature, flow rates, and so forth.

The pre-digestion treatment chamber 12 includes a heater 26 to heat a liquid suspension of solid waste to a desired pre-digestion temperature. A variety of different heater configurations may be used including, but not limited to a sleeve heater, in-line heater or a heater provided within the walls of the pre-digestion treatment chamber 12. The heater 26 may be integral or separate from the pre-digestion treatment chamber 12. In some non-limiting embodiments, the heater heats the liquid suspension of solid waste to a temperature in the range from about 85° to about 150° F. The temperature may be adjusted to optimize the selected pre-digestion treatment to the waste solids.

The pre-digestion treatment chamber 12 may include one or more mixers 28 to mix the suspension of solid waste within the treatment chamber 12.

All of the various pre-digestion processes mentioned above are intended to further reduce the intact molecules to fragmentation and creation of volatile solids to improve the yield of gas and the destruction of the solids in the mixture. Current solids analysis shows 60-65% destruction of solids or from a 12% influent, a 4.2% solids (as total solids and total suspended solids [TS and TSS]) in the effluent, post digestion to a value employing this technology of 75-80% destruction of solids, or a final effluent of 2.4% from a 12% solids influent. Ultimately, this would mean much lower amount of waste solids to be processed in the final effluent water treatment, but substantially higher methane gas values from the solids.

Further, the need for direct feed of additional solid waste substrates (cheese whey or solids, sugar wastes, etc.) can be handled with either in the aerobic pre-digestion treatment chamber or could also be predigested in separate systems and then added to the suspension of solid waste for anaerobic digestion. This modification is unique to the anaerobic digestion system designed herein because it permits on site management of the ancillary wastes for additional gas generation. The process can be designed to accommodate nearly any digestable waste with management of the wastes by destruction prior to the addition to the aerobic zone of the pre-digestion treatment chamber or within the aerobic zone of the pre-digestion treatment chamber. The important element here is the complete control of the influent to the anaerobic digester as well as the conditions within the digester during the anaerobic phase of digestion. Ancillary substrates are the "booster" of the digesters ability to produce methane and presentation of those substrates as a multi-component system for digestion is very useful.

The apparatus for the anaerobic digestion of solid waste 10 includes an anaerobic digester chamber 30. The schematic representation shown in FIG. 1 includes four parallel lanes, designated as anaerobic digester lanes 32-38. The number of lanes may vary. It is not required that the anaerobic digester include multiple lanes, but there may be operational benefits when using multiple lanes such that if one or more lanes needs to be temporarily shut down, other lanes remain operating to continue processing waste solids. It is understood that the features and structures illustrated in the different digester lanes 32-38 of FIG. 1 are representative and not restrictive. It is expected that each of the lanes will be configured with the same features and structures as the other lanes. However, it is within the scope of the invention to configure the lanes differently. For example, the heating and mixing configuration of exterior lanes may differ from heating and mixing configurations of interior lanes. Similarly, multiple lanes may provide flexibility and expansion for use of different feed stocks or replacement of feed stocks. For example, one lane may be configured for the anaerobic digestion of one type of feed stock and another lane may be configured for a different type of feed stock.

Figure 5:
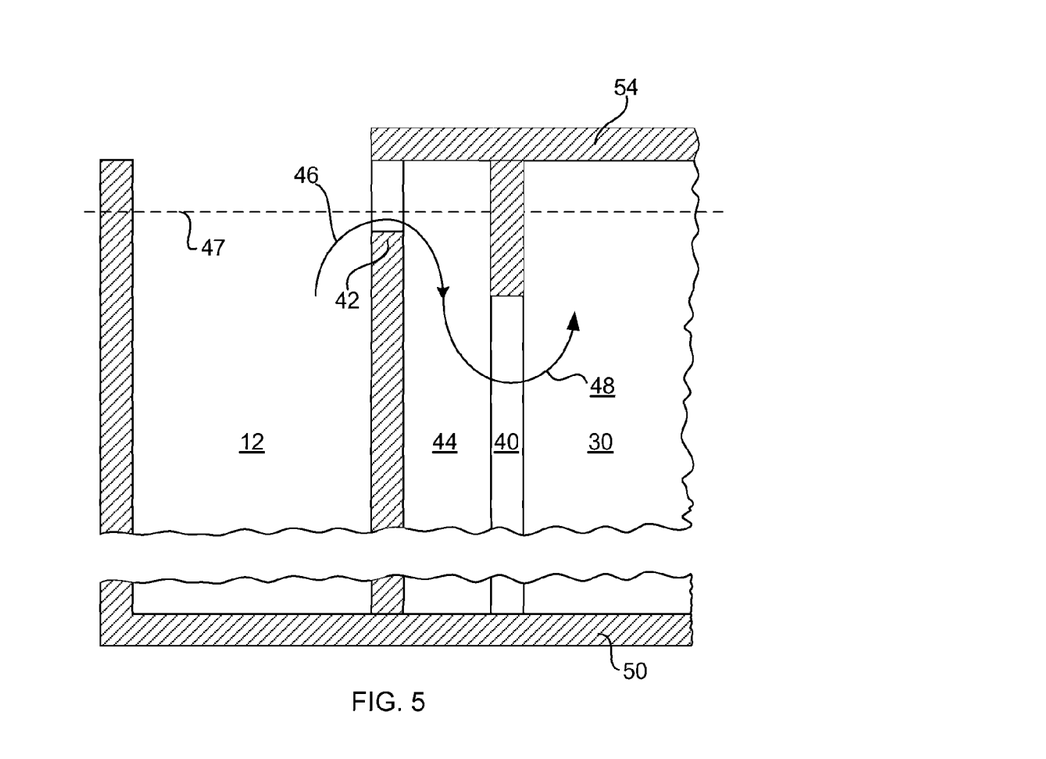
FIG. 5 is a cross-sectional representation showing details of a pre-digestion treatment chamber, weir, and inlet to the anaerobic digester.
Figure 6:
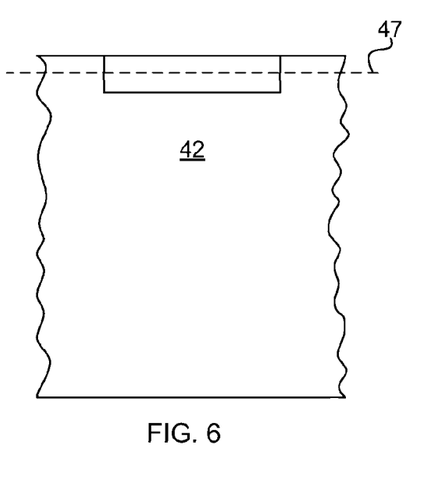
FIG. 6 is a cross-sectional detail of the weir.
Figure 7:
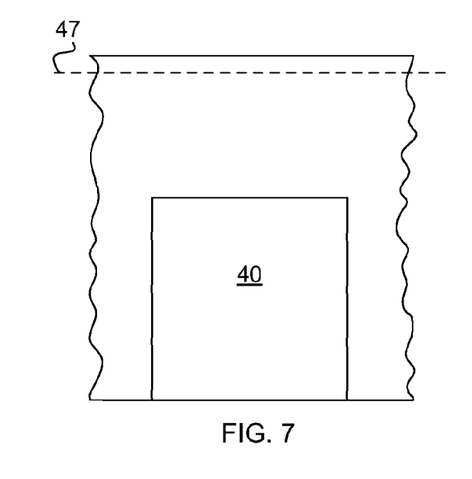
FIG. 7 is a cross-sectional detail of the inlet to the anaerobic digester.

In some embodiments, the anaerobic digester chamber 30 is coupled to the pre-digestion treatment chamber 12 at a digester chamber inlet 40 to receive the pre-treated liquid suspension of solid waste. Because the pre-digestion treatment chamber 12 is exposed to aerobic conditions, the anaerobic digestion chamber 30 must be isolated from the pre-digestion treatment chamber so that oxygen does not enter the anaerobic digestion chamber 30. FIGS. 2 and 5-7 illustrate one possible configuration of structures which function to aerobically isolate the anaerobic digestion chamber 30 from the pre-digestion treatment chamber and which permit flow of the suspension of solid waste into the anaerobic digestion chamber 30. FIG. 5 shows a cross-sectional view of the pre-digestion treatment chamber 12, the anaerobic digestion chamber 30, and the inlet to the anaerobic digester 40. An inlet weir 42 permits a quantity of the suspension of solid waste to flow over the weir 42 into an inlet isolation chamber 44, as shown by arrow 46. The weir is positioned slightly below the fluid level 47. The suspension of solid waste flows from the inlet isolation chamber 44 into the anaerobic digestion chamber 30 through inlet 40, as shown by arrow 48. It is anticipated that mixing of the suspension of solid waste occurs within the pre-digestion treatment chamber 12 and within the anaerobic digestion chamber 30. However, it is presently preferred to minimize any mixing within the inlet isolation chamber 44.

The apparatus for the anaerobic digestion of solid waste 10 is illustrated as a plug flow apparatus, such that the suspension of solid waste moves through the apparatus at the rate undigested source material is input into the apparatus and digested material is removed from the apparatus.

The anaerobic digester chamber 30 will typically include a floor 50, walls 52, and a ceiling 54. Just as the suspension of waste solids must enter the digester chamber 30 without introducing oxygen into the chamber 30, a similar configuration is provided to permit digested solids to exit the chamber 30 without introducing oxygen. Just as the inlet configuration includes an inlet weir 42, inlet isolation chamber 44, and inlet 40, similar structures may be used to permit the digested solids to exit the chamber 30. A digester chamber outlet 56, outlet isolation chamber 58, and outlet weir 60 may be provided. The outlet structures 56, 58, and 60 may have the same basic configuration as the inlet structures shown in FIGS. 5-7. Referring to FIG. 1, the suspension of digested solids pass out of the chamber 30 through the outlet 56, as shown by arrow 62, into the outlet isolation chamber 58, and over outlet weir 60, as shown by arrow 64.

The post anaerobic digester effluent, which includes a suspension of digested waste solids, passes from the outlet isolation chamber into a digester effluent tank 66 for temporary holding and storage of the digester effluent. An effluent outlet 68 is provided to remove the digester effluent from the digester effluent tank 66. In some embodiments, one or more effluent solids analysis sensors 70 or other analytical sensors may measure and identify the effluent content, including non- or poorly-digestible waste solids, percent solids, dissolved and suspended solids, and so forth.

The post anaerobic digester effluent solids that are separated from the liquid fraction and represent a large molecular size, >50 microns for the most part, require that the solids be pathogen free, or substantially so, >99.5% pathogen free. Pathogen is defined as any disease producing agent or microorganism. In the case of manures for example, there are a variety of microorganisms, *streptoccus, klebsiella*, coliform and gram negative bacteria, etc. that are defined as pathogens. Studies have been done demonstrating proof that 6-7 days at 98° F. has destructed more than 97% of the pathogens present in the post digested influents. In the case of a typical residence time within the anaerobic digester of about 16 days, plus or minus 2 days, the destruction of the pathogens will be in the 99+% range. To further destruct pathogens, a sleeve heater, or other heating device, may be added to raise the temperature to 155° F. for a period of 120 seconds to pasteurize the manure before removing the solids for either bedding or for mulching applications. This heating cycle is considered to be 99.99% effective for pathogen reduction.

The anaerobic digester chamber 30 includes one or more gas collection ports 72 to collect methane or bio gas produced in the anaerobic digester.

The anaerobic digester chamber may include heating elements 74 embedded within the floor 50, walls 52, and optionally ceiling 54. The heating elements 74 may be designed to heat specific zones or regions of the digester chamber 30. A plurality of temperature sensors 76 may be dispersed throughout the anaerobic digester chamber 30. A control system 78, which may include control unit 24, may be coupled or electrically connected 79 to the temperature sensors 76 and heating elements 74 to provide continuous, regulated heating of the anaerobic digester chamber 30. The control system 78 may be electrically connected 79 to other sensors, probes, pumps, valves, and system components disclosed herein to provide comprehensive monitoring and control of the anaerobic digestion process. The electrical connection 79 may through any suitable means, including but not limited to, direct wired and wireless connections.

It is anticipated that at least the floor and walls would be constructed of concrete and that the heating system would be embedded in the concrete during construction such that it is ubiquitous in the floor, walls and the potentially ceiling of the entire digester. The system may include a heating or cooling fluid that passes through heat exchange tubing dispersed throughout the floor, walls, and ceiling of the digester. Such a system assures the continuous, regulated heat of the entire digester.

In addition, the disclosed heating system is inexpensive and redundancy can be built into the system so that mean times between failures (MTBF's) are measured as 20 years, or longer. Heating of a digester is an important factor in digester design, and given the wide expanse of temperature ranges in the United States and overseas, from subzero to tropical locations, a design where the temperature regulation can be held at precise values is unique, novel and innovative.

Figure 3:
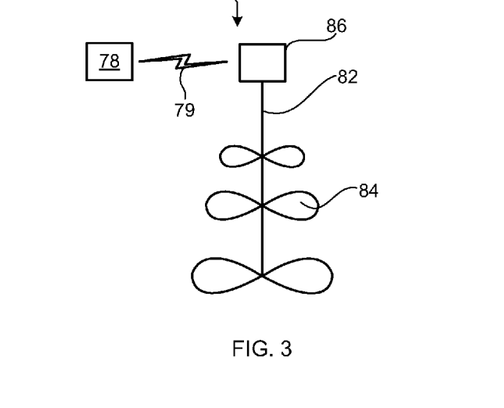
FIG. 3 is a schematic representation of a variable speed mixer.
Figure 4:
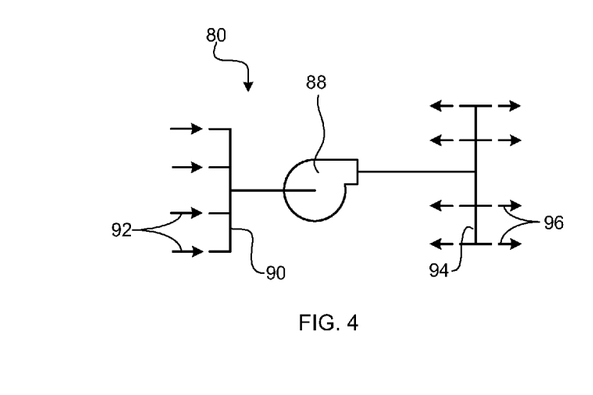
FIG. 4 is a schematic representation of a peristaltic pump mixer.

The anaerobic digester chamber 30 includes a plurality of mixers 80 dispersed throughout the anaerobic digester chamber 30 to mix the suspension of solid waste. As shown in FIG. 1, in one non-limiting embodiment, three mixers 80 are dispersed along the anaerobic digester chamber 30. FIGS. 3 and 4 illustrate non-limiting examples of mixers 80. FIG. 3 shows a variable speed mixer 82. The variable speed mixer includes one or more sets of mixing vanes 84 which are driven by a motor 86. The motor 86 is preferably electrically connected 79 to control system 78 which controls the operation and mixing speed of the mixer 82. In some embodiments within the scope of the invention, the mixing is slow near the inlet 40 and progressively becomes faster near the outlet 56. Thus, mixers 82 disposed closest to the digester chamber inlet 40 may operate at a slower speed than the mixers disposed closest to the digester chamber outlet 56.

FIG. 4 is a schematic representation of a peristaltic hose pump 88. A peristaltic hose pump collects the suspension of waste solids from various locations within the digester chamber 30 and delivers the suspensions to multiple locations within the chamber 30. For example, as shown in FIG. 4, the peristaltic hose pump 88 includes a suction manifold 90 with one or more inlets 92. The inlets 92 will typically be located near the bottom of the digester chamber 30. The peristaltic hose pump 88 includes a discharge manifold 94 with one or more outlets 96. The outlets 96 will typically be located at points near the top of the digester chamber 30.

In one embodiment, the peristaltic hose pumps 88 are fixed to the ceiling of the digester and the hoses are flexible in construction and the hoses attach to a fixed series of pipes with valves (to prevent any air entering into the system during replacement of the hoses) to operate every 20-40 minutes on a rotating basis. The fixed pipes cycle to pick up the liquid/solid portion and redeliver the liquid/solid portion to the surface, thus preventing any solid settling near the base and walls of the unit during the retention span of the digester.

The anaerobic digester chamber may include a plurality of chemical inlets 98 to inject one or more chemical or biological additives at desired locations within the anaerobic digester chamber. Non-limiting examples of such additives include acids or bases for pH control, microbial innoculum, nutrients to support microbial growth, defoaming and/or antifoaming agents, water, and so forth. As shown in FIG. 1, the chemical inlets 98 may be configured as a liquid spray system 100 disposed at the ceiling.

The anaerobic digester chamber 30 may include a plurality of pH sensors 102 dispersed throughout the anaerobic digester 30. The plurality of chemical inlets 98 are preferably coupled to the control system 78 and introduce acid or base to the suspension of solid waste to control the pH based upon pH measurements from the pH sensors. It is within the scope of the digester design to include as many as 12 pH sensors 102 spaced throughout the anaerobic digester and an equal number of temperature sensors 76, spaced a regular intervals. pH control of the system is also useful for the elimination of the potential for foaming (pH<6 and pH>8) being the most likely candidates. However, even if foaming were to happen to any great extent, a defoaming or antifoam agent could be added to reduce or eliminate foam as an issue, using a suitable chemical inlet 98 and spray system 100. Being able to spray the sides and the surface of the digester during digester operations will prevent the formation and/or control the foam levels to below the gas collection ports 72.

A common problem of digesters, especially manure digesters, is that pH is sometimes difficult to control. Even though the digester system disclosed herein has pH control throughout, a potential problem is that foaming can lead to gas contamination by bubbles literally being sucked up into the gas collection ports 72. The gas bubbles come from out of control pH problems associated with certain reactions taking place in the digester. Too much acid created is usually the worse problem. This leads to the generation of excess carbonates and bicarbonates being formed and destructed during the hydraulic retention time in the digester. As one nears the pK (pH 4.7) for the bicarbonates, the $CO_2$ forms and is released not as a byproduct of the enzymatic reaction but as a byproduct of the bicarbonate, much like bubbles in the dishwashing detergents, all bicarbonate based for many years, lots of bubbles meant lots of clean). A so-called skin forms quickly and the trapped gas rises and is sucked into the gas exit ports, causing lots of problems for the water removal system and for the gas quality.

Other sensors (not shown) may be dispersed throughout the digester as needed and coupled to the control system to monitor the digester operation and make appropriate changes to digester operation, such as addition of appropriate chemical or biological additives.

The spray bar system 100 in the inside roof of the digester can provide a more complete cleaning system for digester cleaning. One problem encountered in anaerobic digesters is that they sometimes require being cleaned out. Solids settling, sand and debris are the most common elements found in cleaning out a digester. However, once the digester is "blocked" or incapable of unhindered flow, the need arises to clean them out, usually entailing pulling the top off of the digester, dropping in a front end loader, and scraping the digester clean of the debris, sand, etc. and then recapping and starting the digester flow again. Since the digester design disclosed herein uses mixing of the solid/liquid fractions, a flow of clean water can be used to dilute the solids/liquids from the source additions (e.g. manure or stillage from ethanol plants).

In addition, the design of the anaerobic digester chamber 30 preferably includes a drain 104 disposed in the floor 50 of the digester chamber 30 adjacent the digester outlet 56. To facilitate drainage, the floor 50 is preferably sloped towards the drain 104. The slope may be from 1%-2%, front to back of the digester along the entire digester's length. The drain is connected to a wet well 106 before being pumped to a storage or processing lagoon. A suitable valve 108 isolates the drain from the wet well 106. Clean water can be flushed through the spray system 100 and into the digester, all water directed to the areas requiring cleaning and flushing. The drain pipe may be a 16" pipe, but the digester design is not limited to this size. A pipe of this size would be capable of removing an entire digester (assuming 18.35 ft tall [slope of 2.7 feet over the 180 foot length], 35 foot wide and 180 feet long, or 855,477 gallons total volume retention) in less than 24 hours without ever removing the top of the digester nor requiring any extraordinary measures be taken. In fact, under extreme conditions, the entire digester could be cleaned out in less than 12 hours, beginning to end. This is a huge difference from the current technology of removing the digester top to clean. If the digester is providing either electricity or gas, the entire down time of 24 hours is less than 0.3% of the total time and therefore would save a lot of money from penalties for downtime due to cleaning that would jeopardize the 5% total down time for say the electric company, a penalty for greater than 5% down time.

This labor, money and time saving device is important for the digester design. It is a life line for the operator to shutdown and restart a system within 24 hours and making gas again within the 3-4 days after refilling and equilibrating the digester.

Figure 2:
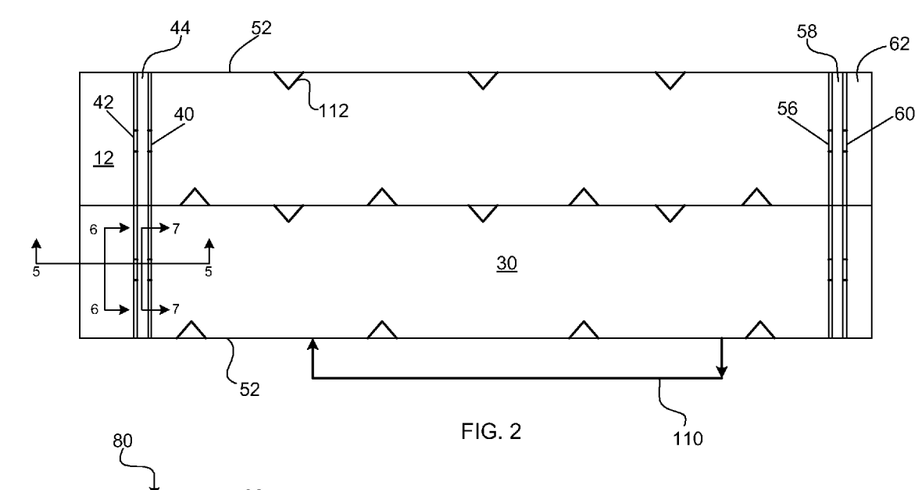
FIG. 2 is a schematic representation of another apparatus for the anaerobic digestion of solid waste.

In some embodiments, the anaerobic digester chamber may include a recycle conduit 110, shown in FIG. 2, connecting the last quadrant of the digester chamber 30 to the first quadrant of the digester chamber under completely anaerobic conditions. This provides an additional "inoculum" boost to the front end of the digester by taking solids and liquids containing the bacterial rich effluent and returning the bacterium to the front end for reuse and additional gas production.

To improve mixing a solids flow through the anaerobic digester chamber, a plurality of triangular deflecting plates 112 may be disposed along the walls of the digester. The triangular deflecting plates preferably have a surface that provides points of attachment for bacteria to collect, multiply, and flourish. In addition to providing improved bacterial growth, the triangular deflecting plates 112 deflect the fluid path to create eddies and currents within the digester chamber 30. The deflection is essentially a side to side directional flow. If the deflecting plates 112 are spaced evenly, and assuming a digester length of 175 feet then every 21.875 feet from the entry to the exit of the digester, a triangular deflecting plate stands 17 feet tall, the angle to be 45° from the wall, extending 8 feet from the wall on the two exposed sides and 11.3 feet between the angles. There are 8 of these triangular deflecting plates in the 175 length of the digester. Of course, this removes 42,813 gallons from the total volume, making the design parameter for total volume actually, 727,712 total gallons.

As mentioned above, triangular deflecting plates are preferably coated with a material or coating to provide points of attachment of the bacteria, for growth and flourishing. The coating is preferably easy to apply and to maintain under anaerobic conditions. For example, the coating may be fiberglass, corrugated steel composition, spray coating on a metal substrate or any materials of construction that would allow for the attachment of the bacteria to the surfaces. So, therefore, flow and surface composition are designed for maximum exposure of the surface area to the liquid/solid influent materials. The rationale for the triangular design is to prevent the collection of solids that otherwise might happen with walls or baffles constructed at right angles.

While the foregoing features have been discussed in relation to FIGS. 1-7, it will be appreciated that the anaerobic digester design disclosed herein may include innovative combinations of any or all of the above features, systems and novel modifications added to make the digester perform beyond current production levels of methane or biogas production. The economic advantages are several, a lower cost of manufacture, a higher input of manure or source materials and the ability to modify a digester to perform from one source material to another. For example, a standard digester of nearly any design would be used for one singular purpose, say for example, manure digestion. In contrast, the new design disclosed herein can be employed to digest a variety of different source materials such as manure, but also modified with little or no cost to handle by-products or another entire new source, e.g. ethanol production waste (corn, sorghum, cellulosics or cane sugars).

One non-limiting design for the digester is a plug flow design having a length to width ratio in the range from 4:1 to 9:1. In one presently preferred embodiment, length to width ratio is about 5:1. That is for every five (5) feet in length, the digester unit is one (1) foot in width. A typical digester having a length to width ratio described herein may be 35 feet wide and 175 feet long. The height is preferably less than or equal to 19 feet, with a 17 foot level of the liquids and solids and a 2 foot gas collection area above the liquid/solid level. It will be appreciated that these sizes can be varied somewhat and still provide a usable anaerobic digester. The volume of a single pass digester of the foregoing dimensions would then be 104,125 cubic feet ($ft^3$) or 770,525 gallons of liquid/solid mass. The gas collection area is then 12,250 $ft^3$. All construction is concrete and the unit sits below the grade of the land (underground).

While specific embodiments of the present invention have been illustrated and described, numerous modifications come to mind without significantly departing from the spirit of the invention, and the scope of protection is only limited by the scope of the accompanying claims.

The invention claimed is:

1. An apparatus for the anaerobic digestion of solid waste comprising:
a pre-digestion treatment chamber wherein a liquid suspension of solid waste is heated to a desired pre-digestion temperature and exposed to aerobic conditions, wherein the pre-digestion treatment chamber comprises one or more inlets to add one or more chemical or biological additives as needed to the suspension of solid waste selected to provide a desired C:N ratio in the solid waste and to improve the anaerobic digestibility of the solid waste; and
an anaerobic digester chamber coupled to the pre-digestion treatment chamber at a digester chamber inlet to receive the liquid suspension of solid waste, said anaerobic digester chamber comprising:
a floor, walls, and a ceiling;
a digester chamber outlet wherein a suspension of digested waste solids exit the digester; and
one or more gas collection ports to collect gas produced in the anaerobic digester.

2. The apparatus according to claim 1, wherein the pre-digestion treatment chamber heats the liquid suspension to a temperature in the range from about 85° to about 150° F.

3. The apparatus according to claim 1, wherein the one or more chemical or biological additive comprises a carbon-rich waste product to increase the carbon content of the solid waste.

4. The apparatus according to claim 1, wherein the one or more chemical or biological additive comprises a nitrogen-rich material to increase the nitrogen content of the solid waste.

5. The apparatus according to claim 1, wherein the one or more chemical or biological additive comprises one or more enzymes.

6. The apparatus according to claim 5, wherein the one or more enzymes are selected to destruct poorly-digestible components of the solid waste.

7. The apparatus according to claim 5, wherein the one or more enzymes are selected from cellulase, hemicellulase, and lipase.

8. The apparatus according to claim 5, wherein the one or more enzymes are selected from proteases, ligninases, laccases, and ureases.

9. The apparatus according to claim 1, wherein the pre-digestion treatment chamber has a volume equivalent selected to provide a retention time in the range from approximately 8 hours to 48 hours based upon the flow rate of the liquid suspension of solid waste.

10. The apparatus according to claim 1, wherein the one or more chemical or biological additive comprises a surfactant.

11. The apparatus according to claim 1, wherein the pre-digestion treatment chamber further comprises one or more chemical sensors to measure total carbon and total nitrogen content of the solid waste.

12. The apparatus according to claim 11, wherein the one or more chemical sensors provide chemical analysis in real time.

13. The apparatus according to claim 11, wherein the one or more chemical sensors further measure total phosphorus content of the solid waste.

14. An apparatus for the anaerobic digestion of solid waste comprising:
a pre-digestion treatment chamber wherein a liquid suspension of solid waste is heated to a desired pre-digestion temperature and exposed to aerobic conditions, wherein the pre-digestion treatment chamber comprises one or more inlets to add one or more chemical or biological additives to the suspension of solid waste to improve the anaerobic digestibility of the solid waste; and
an anaerobic digester chamber coupled to the pre-digestion treatment chamber at a digester chamber inlet to receive the liquid suspension of solid waste, said anaerobic digester chamber comprising:
a floor, walls, and a ceiling;
heating elements embedded within the floor and walls;
a plurality of temperature sensors dispersed throughout the anaerobic digester chamber;
a control system coupled to the temperature sensors and heating elements to provide continuous, regulated heating of the anaerobic digester chamber;
a plurality of mixers dispersed throughout the anaerobic digester chamber to mix the suspension of solid waste;
a plurality of chemical inlets to inject one or more chemical or biological additives at desired locations within the anaerobic digester chamber;
a plurality of pH sensors dispersed throughout the anaerobic digester and coupled to the control system;
a digester chamber outlet wherein a suspension of digested waste solids exit the digester;
a drain disclosed in the floor adjacent the digester outlet, wherein the floor is sloped towards the drain to facilitate drainage; and
one or more gas collection ports to collect gas produced in the anaerobic digester.

15. The apparatus according to claim 14, wherein the pre-digestion treatment chamber heats the liquid suspension to a temperature in the range from about 85° to about 150° F.

16. The apparatus according to claim 14, wherein the one or more chemical or biological additives are selected to provide a desired C:N ratio in the solid waste.

17. The apparatus according to claim 16, wherein the one or more chemical or biological additive comprises a carbon-rich waste product to increase the carbon content of the solid waste.

18. The apparatus according to claim 16, wherein the one or more chemical or biological additive comprises a nitrogen-rich material to increase the nitrogen content of the solid waste.

19. The apparatus according to claim 14, wherein the one or more chemical or biological additive comprises one or more enzymes.

20. The apparatus according to claim 19, wherein the one or more enzymes are selected to destruct poorly-digestible components of the solid waste.

21. The apparatus according to claim 19, wherein the one or more enzymes are selected from cellulase, hemicellulase, and lipase.

22. The apparatus according to claim 19, wherein the one or more enzymes are selected from proteases, ligninases, laccases, and ureases.

23. The apparatus according to claim 14, wherein the pre-digestion treatment chamber has a volume equivalent selected to provide a retention time in the range from approximately 8 hours to 48 hours based upon the flow rate of the liquid suspension of solid waste.

24. The apparatus according to claim 14, wherein the one or more chemical or biological additive comprises a surfactant.

25. The apparatus according to claim 14, wherein the pre-digestion treatment chamber further comprises one or more chemical sensors to measure total carbon and total nitrogen content of the solid waste.

26. The apparatus according to claim 25, wherein the one or more chemical sensors provide chemical analysis in real time.

27. The apparatus according to claim 25, wherein the one or more chemical sensors further measure total phosphorus content of the solid waste.

28. The apparatus according to claim 14, wherein the temperature of the anaerobic digester chamber is regulated to a temperature in the range from about 90° F. to 145° F. (32.2° C. to 62.8° C.).

29. The apparatus according to claim 14, wherein the temperature of the anaerobic digester chamber is regulated to a temperature in the range from about 90° F. to 110° F. (32.2° C. to 43.3° C.).

30. The apparatus according to claim 14, wherein the temperature of the anaerobic digester chamber is regulated to a temperature in the range from about 120° F. to 145° F. (48.9° C. to 62.8° C.).

31. The apparatus according to claim 14, wherein the anaerobic digester chamber further comprises a plurality of triangular deflecting plates.

32. The apparatus according to claim 31, wherein the triangular deflecting plates have a surface that provides points of attachment for bacteria.

33. The apparatus according to claim 14, wherein the anaerobic digester chamber is configured for plug flow of the suspension of solid waste.

34. The apparatus according to claim 33, wherein the anaerobic digester chamber has a length to width ratio in the range from 4:1 to 9:1.

35. The apparatus according to claim 14, wherein the plurality of chemical inlets are coupled to the control system and introduce acid or base to the suspension of solid waste to control the pH based upon pH measurements from the pH sensors.

36. The apparatus according to claim 14, wherein the liquid spray system sprays a chemical defoamer and/or antifoamer.

37. The apparatus according to claim 14, wherein the liquid spray system sprays water.

38. The apparatus according to claim 14, wherein the plurality of mixers comprise peristaltic hose pumps.

39. The apparatus according to claim 14, wherein the plurality of mixers comprise variable speed mixers.

40. The apparatus according to claim 39, wherein the mixers disposed closest to the digester chamber inlet operate at a slower speed and progressively increase in speed such that the mixers disposed closest to the digester chamber outlet operate at a faster speed.

41. The apparatus according to claim 14, further comprising a recycle conduit connecting the last quadrant of the digester chamber to the first quadrant of the digester chamber.

42. A process for the anaerobic digestion of solid waste comprising:
    preheating a liquid suspension of solid waste;
    exposing the suspension of solid waste to aerobic conditions in a pre-digestion treatment chamber;
    measuring total carbon and total nitrogen content of the solid waste in the pre-digestion treatment chamber;
    adding one or more chemical or biological additive as needed to the suspension of solid waste in the pre-digestion treatment chamber to provide a desired C:N ratio in the solid waste and/or to destruct a poorly-digestible component of the solid waste;
    introducing the suspension of solid waste into an anaerobic digester to anaerobically digest the solid waste;
    controlling the temperature of the suspension of solid waste in the anaerobic digester to a temperature in the range from about 90° F. to 145° F. (32.2° C. to 62.8° C.);
    controlling the pH of the suspension of solid waste in the anaerobic digester to a pH in the range from about 5 to 9;
    mixing the suspension of solid waste; and
    recovering methane gas produced by the anaerobic digester.

43. The process according to claim 42, wherein the one or more chemical or biological additive comprises a carbon-rich waste product to increase the carbon content of the solid waste.

44. The process according to claim 42, wherein the one or more chemical or biological additive comprises a nitrogen-rich material to increase the nitrogen content of the solid waste.

45. The process according to claim 42, wherein the one or more chemical or biological additive comprises one or more enzymes.

46. The process according to claim 45, wherein the one or more enzymes are selected to destruct the poorly-digestible component of the solid waste.

47. The process according to claim 45, wherein the one or more enzymes are selected from cellulase, hemicellulase and lipase.

48. The process according to claim 45, wherein the one or more enzymes are selected from protease, ligninase, laccase, and urease.

49. The process according to claim 42, wherein the one or more chemical or biological additive comprises a surfactant.

50. The process according to claim 42, further comprising the steps of:
    removing non-digested solids from the anaerobic digester; and
    analyzing the non-digested solids to identify the poorly-digestible component.

* * * * *